(12) United States Patent
Noras

(10) Patent No.: US 9,801,586 B2
(45) Date of Patent: Oct. 31, 2017

(54) DEVICE FOR THE, IN PARTICULAR, TRANSPERINEAL EXAMINATION OF PATIENTS

(71) Applicant: Hubert Noras, Würzburg (DE)

(72) Inventor: Hubert Noras, Würzburg (DE)

(*) Notice: Subject to any disclaimer, the term of this patent is extended or adjusted under 35 U.S.C. 154(b) by 577 days.

(21) Appl. No.: 14/380,946

(22) PCT Filed: Nov. 15, 2013

(86) PCT No.: PCT/DE2013/100385
§ 371 (c)(1),
(2) Date: Aug. 26, 2014

(87) PCT Pub. No.: WO2014/079415
PCT Pub. Date: May 30, 2014

(65) Prior Publication Data
US 2015/0065862 A1    Mar. 5, 2015

(30) Foreign Application Priority Data
Nov. 23, 2012 (DE) .................. 10 2012 022 834

(51) Int. Cl.
*A61B 5/00* (2006.01)
*A61B 5/055* (2006.01)
(Continued)

(52) U.S. Cl.
CPC ............ *A61B 5/702* (2013.01); *A61B 5/0555* (2013.01); *A61G 13/129* (2013.01);
(Continued)

(58) Field of Classification Search
CPC .............. A61B 5/702; A61B 5/0555; A61B 2017/00274; A61B 6/04; A61G 13/129;
(Continued)

(56) References Cited

U.S. PATENT DOCUMENTS 5,517,991 A * 5/1996 Herrmann .......... A61B 17/2255
378/209
5,871,448 A   2/1999 Ellard
(Continued)

FOREIGN PATENT DOCUMENTS

WO    WO2009000321 A1    12/2008

OTHER PUBLICATIONS

Eur Radiol (2012) 22:189-1835 (as cited on p. 1, lines 15-22 of the present application).
(Continued)

*Primary Examiner* — David E Sosnowski
*Assistant Examiner* — Myles Throop
(74) *Attorney, Agent, or Firm* — Westman, Champlin & Koehler, P.A.

(57) ABSTRACT

Apparatus for the, in particular, transperineal examination of patients, consisting of two leg holders (1) arranged symmetrically in relation to the longitudinal axis of the patient, wherein the leg holders (1) have arranged between them a carriage (2) which runs parallel to the center plane of the patient and can be displaced, and arrested, in the direction of the longitudinal axis and, at its patient end, has a frame (3) which is oriented perpendicularly to the displacement direction and is suitable for accommodating a grid (4) and/or a targeting device or an NMR coil.

12 Claims, 1 Drawing Sheet

(51) Int. Cl.
*A61G 13/12* (2006.01)
*A61G 13/00* (2006.01)
*A61G 13/10* (2006.01)

(52) U.S. Cl.
CPC ...... *A61G 13/1245* (2013.01); *A61G 13/0009* (2013.01); *A61G 13/101* (2013.01)

(58) Field of Classification Search
CPC .............. A61G 13/1245; A61G 13/101; A61G 13/0009; A61G 13/0018
USPC ................... 606/130; 600/415, 422; 128/891
See application file for complete search history.

(56) References Cited

U.S. PATENT DOCUMENTS

| | | | | |
|---|---|---|---|---|
| 5,957,935 A * | 9/1999 | Brown | ............... | A61B 17/3403 600/437 |
| 6,202,230 B1 * | 3/2001 | Borders | ............. | A61G 13/0009 5/613 |
| 6,378,149 B1 * | 4/2002 | Sanders | ............... | A61B 6/0442 378/209 |
| 6,598,275 B1 * | 7/2003 | Kolody | ................ | A61G 13/101 24/455 |
| 2004/0133979 A1 | 7/2004 | Newkirk | | |
| 2006/0117485 A1 * | 6/2006 | Brophy | .............. | A61G 13/0009 5/624 |
| 2008/0216239 A1 * | 9/2008 | Luginbuhl | ........... | A61B 5/0555 5/601 |
| 2009/0235457 A1 * | 9/2009 | Harvey | .............. | A61G 13/0009 5/624 |
| 2012/0046540 A1 * | 2/2012 | Branch | ................ | A61B 5/1036 600/415 |
| 2014/0081181 A1 * | 3/2014 | Branch | ................. | A61B 5/702 600/595 |

OTHER PUBLICATIONS

International Search Report (ISR) with regard to PCT/DE2013/100385 as completed by the EPO on Feb. 27, 2014 and dated Mar. 7, 2014.

* cited by examiner

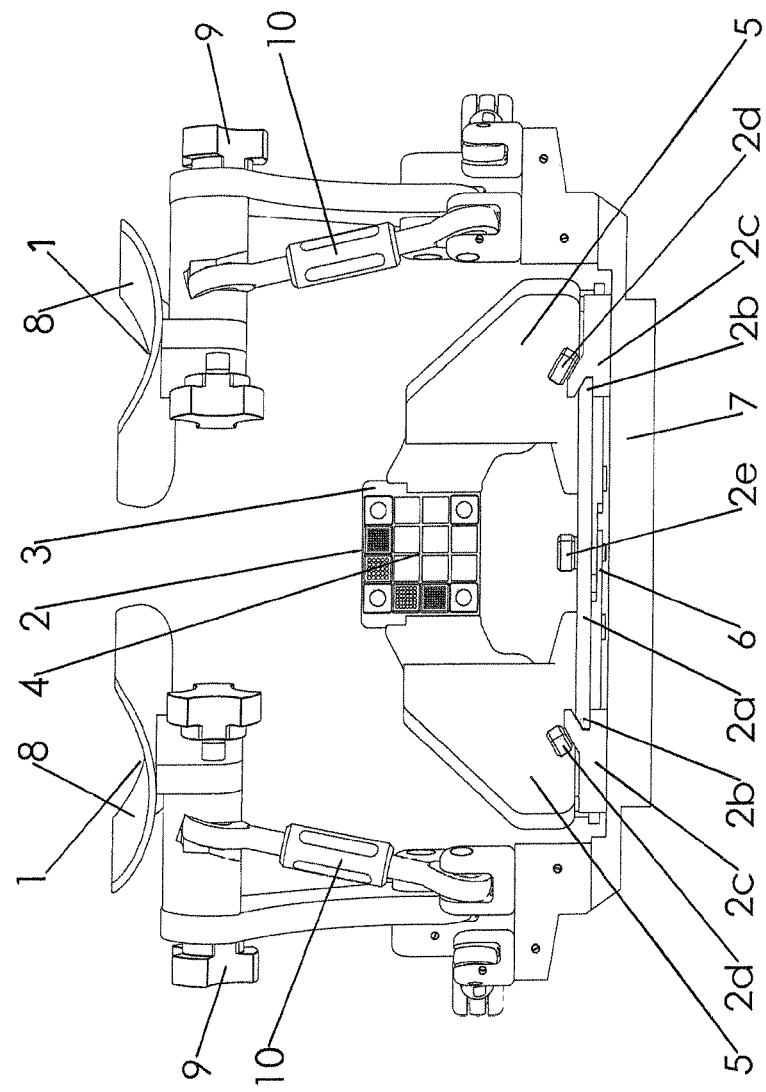

DEVICE FOR THE, IN PARTICULAR, TRANSPERINEAL EXAMINATION OF PATIENTS

The invention relates to the provision of a device for the in particular transperineal investigation of patients, comprising two leg holders that are disposed symmetrical to the longitudinal axis of the patient.

The issue treated predominantly with the present application is the optimum documenting of diseases of the prostate, in particular of prostate carcinoma, by imaging processes, the removal of tissue samples by biopsy processes and the implementation and performance of operative treatment measures of different kinds. The chief prerequisite for the optimization of the relevant known processes is to create the optimum prerequisites for performing the above-described steps (performing imaging processes, biopsy and operative interventions for therapeutic purposes).

In the context of a recently issued publication in Eur Radiol (2012) 22:1929-1835 (European Society of Radiology 2012), a device is described in which the patient on a recliner is transported into the NNMR tube, which has two leg supports, the patient, thus lying on the device, is in a position that is comparable to the known arrangements on a gynecological chair, but with the essential different that the chair is tilted backwards by 90°, that is to say the chair backrest is horizontal and introduced into the tube through a slit. The legs are supported by leg holders in the region of the knee and lower leg. Such treatment chairs are additionally also generally known, outside the area of gynecology, in the field of urology.

The creation of optimum work conditions is a prerequisite for the achievement of the best possible work results. This includes the fact that the perineal area, which, as that region of the pelvis that is defined between thighs, is as spaciously accessible as possible, to allow the introduction of coils and/or the removal of tissue samples by the introduction of biopsy needles and/or of surgical instruments to be performed as favorably as possible. Solving this problem is problematic in the case of adipose patients and, in particular, those with a large diameter of the thighs. In the field of gynecology, as well as of urology, this problem is solved in that the thighs are opened by spreading the leg holders wide enough apart, that is to say the opening angle is chosen so as to be sufficiently large, to achieve the sought optimum accessibility. Due to the possibility of making the opening angle of the legs free, sufficiently satisfactory working conditions can be achieved, even with extremely thick thighs, in order to make the perineum accessible to perform the above-described measures.

Such devices and the choice of even relatively large opening angles cannot be implemented in many cases, since the corresponding measures to be performed must be performed in an NMR tomography device of conventional design and, due to the tubular shape, in which the patient is to be introduced during the diagnostic and therapeutic measures, the possibility of opening the thighs is limited by the geometry of the tube of the NMR device.

The conventional examination method in case of suspicion of a prostate carcinoma is as follows: the basis and cause of a more detailed examination is an elevated PSA value, which is to be evaluated as suspicion of the presence of a prostate carcinoma. Conventionally, the next step then consists in taking tissue samples by way of biopsy and examining them histologically to confirm or refute the suspicion. The problem is that, on the basis of ultrasound diagnostics, a determination of the location and the regional extent of the suspect tissue cannot be reliably delimited from healthy tissue, so that the removal of a plurality of tissue samples becomes necessary. A considerable advance here is brought by the application of imaging procedures based on NMR technology, which makes possible a reliable isolation and identification of the suspected tissue to be biopsied from the healthy tissue. For this reason, it is part of the most up-to-date and modern practice, to remove the suspect tissue under an NMR-controlled prostate biopsy. It does not require closer and more detailed justification that the performance of a plurality of biopsies is to be regarded as of considerable disadvantage.

On this basis, it is the aim of the invention to provide a device with the aid of which the examination and treatment of the prostate carcinoma can be considerably facilitated.

This object is achieved according to the invention in that between the leg holders (1), there is arranged a carriage (2) which runs parallel to the center plane of the patient and can be displaced and locked, in the direction of the longitudinal axis and, at its patient end, has a frame (3) that is oriented perpendicular to the displacement direction and is suitable for receiving a grid (4) and/or a target device or an NNMR coil.

The device proposed according to the invention, in its basic construction, consists of three elements. On one hand, a leg holder is present, which is designed in the form of a half-shell to receive the patient's lower leg, and a foot, on which the half-shell rests. Symmetrical to this described leg holder, as a second element, a further leg holder of essentially the same construction exists, which is arranged symmetrically to the first leg holder. The axis of symmetry is described by the longitudinal axis of the patient. As a third, finally, a carriage that can be moved essentially in a horizontal direction is present, at the upper end, that is to say the end close to the patient, of which, a frame is fastened. The frame is positioned such that it comes to lie in that pelvis region that is located between the inner surfaces of the thighs. The application of the proposed device is thus principally provided for transperineal application, which, in special cases, however, does not in principle exclude the use of transgluteal or transrectal interventions. The device proposed according to the invention is thus also suitable for gynecological purposes and for examinations of the rectum. It can be seen as an essential of transperineal access that the administration of antibiotics, as is inevitably necessary through the intestine (transrectal access) in the case of biopsies, is superfluous.

The frame is designed such that it is capable of receiving various elements and allowing them to be exchanged. This includes expressly the grid, through the use of which, the sample is fixed and on the other hand, due to the grid-like openings there is the possibility of passing biopsy needles through the grid and inserting them such that they are accurately positioned. The procedure is usually as follows: first, the position of the suspect tissue is determined by NMR techniques and exactly measured and the coordinates are determined. The ascertained coordinates are used to determine the grid opening which the medical instrument, for example the biopsy needle, must penetrate. The coordinates can further serve to determine the penetration depth of the instrument. This procedure permits the intervention to the suspect tissue areas to be restricted and tissue to be selectively removed (biopsy) and/or operative interventions to be made.

Irrespective of this, with the application of NMR processes, for purely imaging purposes, a coil can be inserted into the frame, which will contribute to a considerable improvement of the image quality.

The carriage bearing the frame permits the patient to be transferred without hindrance into the treatment position, that is to say the patient to be laid on his back, straightened out and the lower legs to be laid in the leg holder intended therefor. Since during this phase the carriage is in a withdrawn position, that is to say is remote from the patient, this is possible without hindrance. If the patient is then in the end position, the carriage is moved close to him, specifically until the frame with the grids or coils located therein comes to lie in the perineal area because of translatory displacement. Here, the carriage is then fixed for the duration of the examination.

The constructional design of the carriage, in its basic construction, consists of rails, which are oriented in the direction of the patient's center axis, and on which the carriage, with the frame fastened and approximately centered thereon, is located. For temporary fixing of the carriage, fixing means are provided.

The proposed device proves advantageous for the removal of tissue (biopsies) to be examined histologically, for removal of carcinomas after different operative methods and for improving the image quality in the NMR recording method. Without restricting its generality, in the operative methods, cryo methods can be used, which are characterized in that, in the region of the carcinoma, punctures are introduced in an adequate number, so that after introduction of the refrigerant, a destruction of the carcinogenic tissue occurs.

The constructional design of the carriage may be such that, in two mutually opposite edge regions, at least two guide wings are disposed, which engage in rails that are U-shaped in design. The carriage may be temporarily fixed by means of clamping screws.

It was recognized as advantageous that the entire device, comprising the two leg holders and the carriage, is in one piece. In the orientation and adjustment, but also in the setting of the leg holders and carriage, the symmetrical arrangement and synchronous adjustment can be implemented most simply.

In general, finally, the leg holders are provided with adjustment means for adaptation to the different anatomical conditions.

The adjustability of the frame and consequently the grid and coil which are to be received therein permit not only the adaptation to the different anatomical conditions but also readily permits, in departure from the transperineal accessibility of the prostate, which is foremost, also examinations of the gynecological region or of the intestine.

In a further embodiment of the device according to the invention, in order to improve the accessibility of the perineal area for performing the diagnostic and/or therapeutic measures for all patients and in particular for those with corpulent thighs, it is therefore proposed that two-sided pressing jaws are integrated into the device, which are disposed symmetrically to the axis of symmetry defined by the patient's longitudinal axis and move towards the patient and can be reduced in distance. Accordingly, the two pressing jaws describe, in terms of their spatial arrangement, the two legs of an isosceles trapezoid. According to the usual terminology of the geometry, a trapezoid is described as a plane quadrangle with two parallel sides of unequal lengths, the bases, and two non-parallel sides, which are termed legs. When the two legs have identical lengths, the term isosceles trapezoid is used. The application is such that, when they reach the end position, the jaws, essentially in the plane defined by the patient, move outwards perpendicular to the longitudinal axis of the patient and are pressed against the thighs. In dependence on the anatomy and the applied pressure, the inner side, more precisely the elastic volume regions of the thigh, which are determined essentially by the fat and muscle components, are deformed essentially upward and downward with respect to the plane formed by the patient, i.e. perpendicular to said plane, such that a significant improvement of the access to the perineum results. While retaining the position of the longitudinal axis of the thighs, the pressure jaws effect a significant enlargement of the spatial volume available for access to the perineal area. By this means a noticeable improvement of the handling of diagnostic and/or therapy instruments is achieved, consequently an improvement of the work results exists.

The manner of the adjustment of the pressure jaws, that is to say the approach and pressing against the inside of the thigh can take place in different ways. If the patient is in the end position, in which the thighs lie on the leg holders, the pressure jaws are moved against the lower legs. From the point of view of the basic principle, it is immaterial whether a successive approach of the individual pressure jaws against the thighs takes place or whether this takes place in a synchronous movement that is symmetrical and also symmetrical with respect to the longitudinal axis of the patient. From this it follows naturally that, during the phase in which the patient is brought into the end position and also as long as the frame is not yet moved against the perineum, and pressed thereon, the two jaws are relatively close together.

It is regarded as expressly preferred if the moving against and application of the frame against the perineal area by translating a carriage is also used at the same time to move the pressure jaws outwardly with respect to the center axis. To this end, it is provided that the carriage has a mechanical connection with the actuating levers that effect the pivoting of the pressure jaws. In such a case, all movements, namely the pressing of the frame against the perineal area as well as the moving of both pressure jaws outwardly, are synchronous, so that the times of the preparation work can be minimized.

To implement the symmetrical moving apart of the pressure jaws constructionally, it is preferred to provide a scissor mechanism, which ensures that a symmetrical movement is performed.

As a drive for the scissor mechanism, any type of drive is conceivable and in particular also the fact that the movement of the carriage is used for actuating the scissor mechanism.

Further details, features and advantages of the invention can be taken from the following descriptive part, in which an exemplary embodiment of the invention is explained with reference to the drawing, wherein:

FIG. 1 shows the device according to the invention in the longitudinal direction of the carriage.

The top view of the device according to the invention, which is kept diagrammatic, is shown in the direction of movement of the carriage and without the patient.

The device is essentially characterized by two leg holders of equal construction, which are aligned with respect to one another and are oriented symmetrical to the center plane running perpendicular to the plane of the drawing. In between them and specifically also symmetrical to this center plane, a carriage 2 with the frame 3 fastened thereon, in which, in the exemplary embodiment in the drawing, a grid 4 is inserted.

The carriage 2, in the exemplary embodiment shown in the drawing, consists of a horizontally extending plate 2a, which, at its two peripheral ends that lie opposite one another, are provided with guide wings 2b, which, in turn, in each case engage in U-shaped rails 2c that extend perpendicular to the plane of the drawing. For fixing the carriage movement, as is necessary at the stop point of the frame at the perineal area, two fixing screws 2d in each case are located at each side in the region of the rail, which pass through the rail 2c and are capable of firmly clamping the guide wings. Below the plate 2a, a scissor mechanism 6 is indicated, of which one fulcrum is the fastening point 2e of the scissor mechanism 6 on the plate 2a. This scissor mechanism 6, on a displacement of the carriage 2, in the arrangement in the drawing, in the event of a movement toward the patient, has the effect of moving the pressing jaws 5 symmetrically outward and toward one another again with a return movement.

The entire arrangement just described is fixed on a common base plate 7.

The specific embodiment of the leg holder 1 is known from the prior art. On its top side there is in each case a trough-shaped contact surface 8, which is to be dimensioned such that they are approximately adapted to the surface form of the lower leg.

This contact surface 8 can be pivoted about the horizontal axis which runs in the plane of the drawing, and can be fixed by means of locking nuts 9.

The entire arrangement is located on a lever, which is fastened in the region of the base plate 7 so as to be pivotable and thus permits an adaptation to different leg lengths. The angle with respect to the longitudinal axis of the patient is set by means of a pivoting about the vertical axis, which, in the exemplary embodiment shown, takes place in that a cylinder, with one end mounted so as to be stationary and concealed in the present drawing, acts on a point that is located such that it is eccentric with respect to the vertical axis. The actuation of the cylinder leads to a pivoting of the pivot lever about the vertical axis.

To support each leg holder 1, a cylinder 10 is fastened so as to be pivotable at its two corner points. The pivotable arrangement permits, while retaining the support, an adjustment of the leg holder, which naturally has to take place in such a manner that they are individually adapted to the physical proportions of the patient.

As a result, a device is obtained which is especially suitable for use for examination of the prostate and in particular of the prostate carcinoma, the treatment being suitable both for removal of tissue to be histologically examined within the scope of a biopsy, but also for an operative intervention for eliminating the carcinogenic tissue. In the case in which receiving coils are introduced into the frame, an improved image quality can be achieved. It does not require detailed explanation that this device is also suitable for use in gynecology or for performing rectal operations, the adjustability and adaptability of the frame proving of particular advantage.

LIST OF REFERENCE CHARACTERS

1 Leg holder
2 Carriage
  2a Plate
  2b Guide wing
  2c U-shaped rail
  2d Fixing screw
  2e Fastening point of the scissor mechanism
3 Frame
4 Grid
5 Pressing jaw
6 Scissor mechanism
7 Base plate
8 Trough-shaped contact surface
9 Locking nut
10 Cylinder

The invention claimed is:

1. A patient stabilization device, comprising:
    a carriage guidedly movable along a longitudinal axis of said patient stabilization device;
    a first leg holder;
    a second leg holder substantially mirror symmetric to said first leg holder relative to a plane comprising said longitudinal axis;
    an instrument guide frame mounted to said carriage; and
    a thigh spreading device comprising a plate-like first wing and a plate-like second wing, wherein
    said plate-like first wing and said plate-like second wing are guidedly moveable in a direction substantially perpendicular to said plane and form an acute angle with said longitudinal axis.

2. The device of claim 1, wherein said second wing is substantially mirror symmetric to said first wing relative to said plane.

3. The device of claim 1, comprising a mechanism that simultaneously moves said first wing in a first direction substantially perpendicular to said plane and said second wing in a second direction opposite to said first direction.

4. The device according to claim 1, wherein the instrument guide frame is capable of exchangeably receiving a grid and/or target device and/or a NMR tomographic imaging coil.

5. The device according to claim 1, wherein the instrument guide frame and/or the first and second leg holders are adjustable in their spatial orientation.

6. The device according to claim 1, wherein the carriage is movable along rails which extend parallel to the longitudinal direction of the device and can be fixed in any position along the rails.

7. The device according to claim 1, wherein the first and second leg holders and the carriage are integrated with one another as one piece.

8. The device according to claim 1, wherein the first and second wings are movable synchronously outwardly by means of a common drive.

9. The device according to claim 8, wherein the common drive is formed by coupling to the carriage.

10. The device according to claim 1, wherein the first and second wings are in connection with a scissor mechanism.

11. An instrument guiding method; comprising:
    positioning a patient on a patient stabilization device such that a spine of said patient extends substantially along a longitudinal axis of said patient stabilization device;
    positioning a first leg of said patient on a first leg holder of said patient stabilization device;
    positioning a second leg of said patient on a second leg holder of said patient stabilization device, which second leg holder is substantially mirror symmetric to said first leg holder relative to a plane comprising said longitudinal axis;
    spreading a thigh of said first leg from a thigh of said second leg using a thigh spreading device of said patient stabilization device, said thigh spreading device comprising a plate-like first wing and a plate-like second wing, each of said first wing and said second wing forming an acute angle with said longitudinal axis and being guidedly moveable in a direction substantially perpendicular to said plane;

positioning a carriage of said patient stabilization device proximate to a perineal region of said patient, said carriage being guidedly movable along said longitudinal axis; and guiding an instrument using an instrument guide mounted to said carriage.

12. The method of claim 11, wherein:

said spreading comprises simultaneously and symmetrically moving said first wing in a first direction substantially perpendicular to said plane and said second wing in a second direction opposite to said first direction using a mechanism of said patient stabilization device.

* * * * *